United States Patent [19]

Alvarado

[11] 4,047,654
[45] Sept. 13, 1977

[54] SURGICAL STAPLER

[76] Inventor: Alfredo Alvarado, 9114 Dale Road, Philadelphia, Pa. 19115

[21] Appl. No.: 699,027

[22] Filed: June 23, 1976

[51] Int. Cl.² ............................................. B25C 5/02
[52] U.S. Cl. .................................... 227/19; 227/76
[58] Field of Search .................................. 227/19, 76

[56] References Cited

U.S. PATENT DOCUMENTS

| 3,252,643 | 5/1966 | Strekopytov et al. | 227/19 |
| 3,269,631 | 8/1966 | Takaro | 227/19 |
| 3,388,847 | 6/1968 | Kasulin et al. | 227/19 |

*Primary Examiner*—Granville Y. Custer, Jr.

*Attorney, Agent, or Firm*—Seidel, Gonda & Goldhammer

[57] ABSTRACT

Anastomosis of hollow viscera is effected interlumenally by a surgical stapler. The stapler includes an ovoid-shaped staple head and an ovoid-shaped anvil which are mounted on the distal ends of an open ring support structure, the major part of which extends between the head and the anvil externally of the viscera. The staple head includes an ovoid-shaped tensor ring, an ovoid-shaped cutting blade and double ovoid-shaped rows of staple drivers. Closing of the instrument's handle grips moves the stapler head toward the anvil whereby the tissue between the head and the anvil is tensioned and stapled and the area within the rows of staples is cut away by the cutting blade.

11 Claims, 11 Drawing Figures

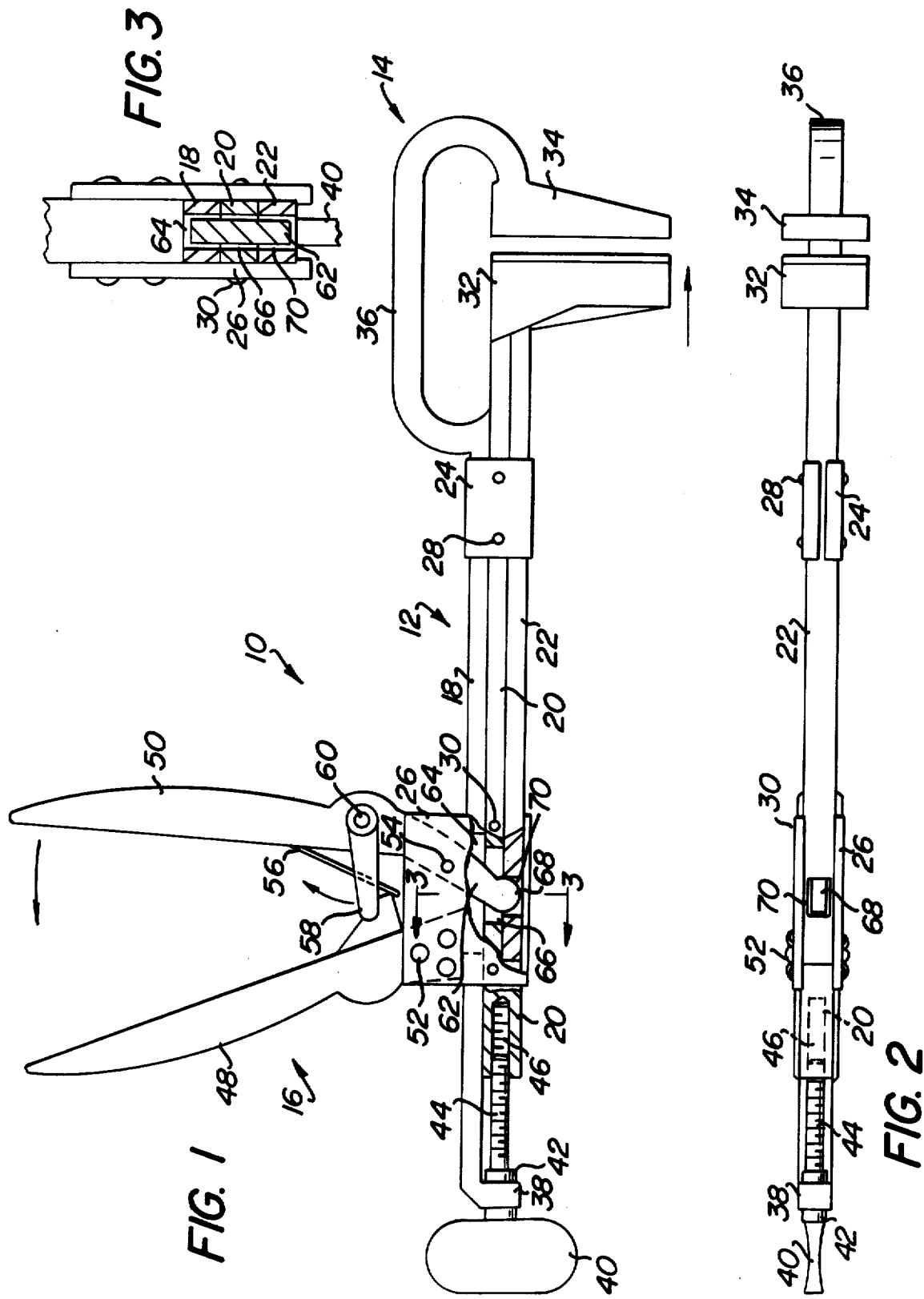

SURGICAL STAPLER

This invention is directed toward a surgical stapler and more particularly toward a surgical stapler which performs an anastomosis of hollow viscera internally of the viscera.

Heretofore, when it was necessary to attach together the ends of vascular or digestive tract organs such as the esophagus or intestines, it was customary to perform this operation manually by the use of a needle and suturing thread. These operations normally required a large number of stitches and the quality of the suture depended primarily on the skill of the surgeon.

Automatic suturing devices utilizing a plurality of metallic staples have been proposed for facilitating this operation. While these devices have met with some success, they have not been totally satisfactory. Because of the design of these previous devices, they also have limited applicability.

The first of these prior art devices were of the linear type and were only capable of forming a linear suture. One such device is described, for example, in U.S. Pat. No. 3,252,643. Since the staplers were capable of making only a linear row of staples, they were substantially limited in use and had limited capabilites. It was possible, for example, to perform an end to end anastomosis of a hollow viscera such as intestines, but this required a plurality of stapling operations using a technique known as triangulation. This procedure was, therefore, rather slow. Furthermore, these devices could not be used for side to side or end to side anastomosis or for various other procedures.

In order to overcome some of these deficiencies of the linear staplers, various circular staplers were developed. Examples of these circular staplers are described in U.S. Pat. Nos. 3,193,165; 3,552,626 and 3,638,652. These staplers are capable of simultaneously setting a complete circular row of staples. While these circular staplers have made it substantially easier to join together hollow viscera, they also have not been totally satisfactory because of the tendency to become jammed.

One of the major drawbacks in the devices such as shown in U.S. Pat. No. 3,193,165 is that the staple head and anvil head are joined together by a rod which is located within the circular row of staples. As a result of this arrangement, the ends of the tubular viscera members which are to be joined together cannot be placed in line with the staples until after the stapler is placed in its proper position. This means that the stapler must first be properly positioned and then held in this position while the tissue is manipulated into position between the staple head and the anvil head. This procedure requires a substantial amount of time which reduces the efficiency of the stapler.

These prior art circular staplers have several other drawbacks. As a result of their shape, and the manner in which they are used, a relatively large incision must be made in the viscera wall for introducing the staple and anvil heads. Furthermore, in use, the anvil and staple heads must be substantially axially aligned with the viscera. Because of this alignment, these prior art devices can only be used to staple together the free ends of tubular shaped viscera which have an internal diameter substantially the same as the outer diameter of the stapler. Even further, it has been found that the cutting knives employed with these prior art staplers have not performed a clean cutting operation.

The present invention overcomes substantially all of the deficiencies of the prior devices described above. The surgical stapler of the present invention performs anastomosis of hollow viscera internally of the viscera wih a single stapling operation. The stapler includes an ovoid-shaped staple head and an ovoid-shaped anvil which are mounted on the distal ends of an open ring support structure. The major part of the support structure extends between the head and the anvil externally of the viscera. The staple head includes an ovoid-shaped tensor ring, an ovoid-shaped stoma-forming cutting blade and double ovoid-shaped rows of staple drivers. The external open ring support allows room for the tensor ring which was impossible with the prior art devices because of the internal rod connecting the staple head to the anvil. Closing of the instrument's handle grips moves the staple head toward the anvil whereby the tissue between the head and anvil is tensioned and stapled and the area within the rows of staples is cut away by the cutting blade.

For the purpose of illustrating the invention, there is shown in the drawings a form which is presently preferred; it being understood, however, that this invention is not limited to the precise arrangements and instrumentalities shown.

FIG. 1 is a side elevational view of a surgical stapler constructed in accordance with the principles of the present invention.

FIG. 2 is a bottom plan view of the device shown in FIG. 1.

FIG. 3 is a sectional view taken along the line 3—3 of FIG. 1.

Figure 4:
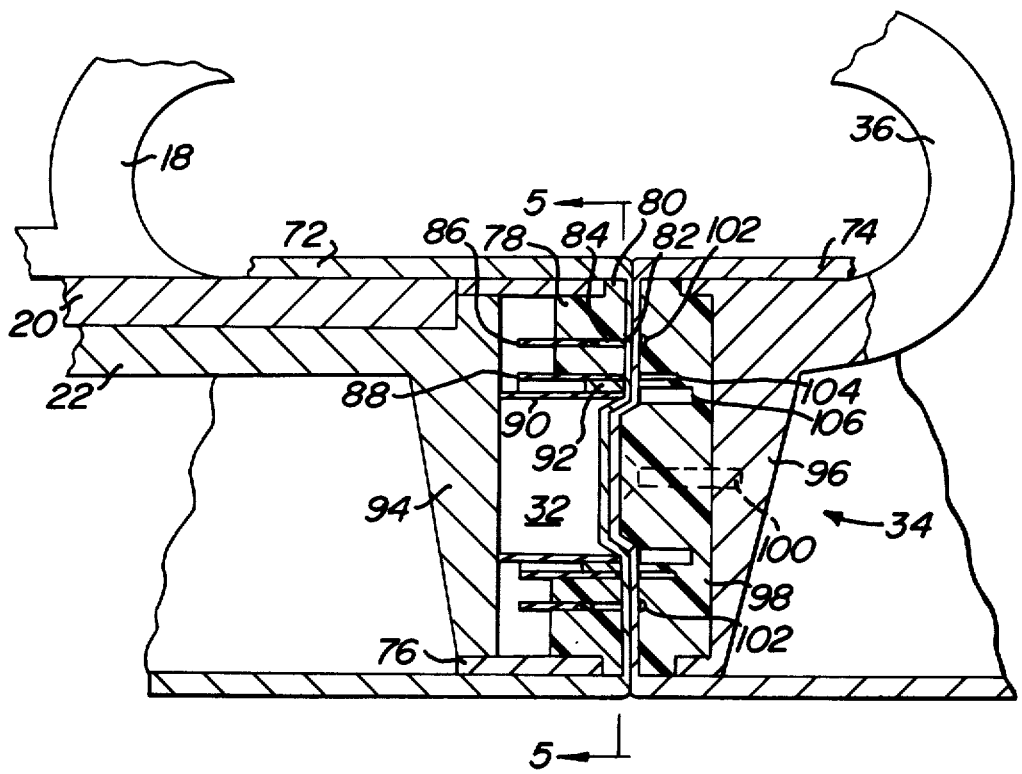
FIG. 4 is an enlarged sectional view showing the details of the staple head and anvil.

Referring now to the drawings in detail wherein like reference numerals are employed to indicate like elements throughout the several figures, there is shown in FIG. 1 a side view of a surgical stapler constructed in accordance with the principles of the present invention and designated generally as 10. Stapler 10 is comprise essentially of three portions; a main body portion 12, a stapling portion 14 and a handle portion 16. Main body portion 12 includes an upper elongated rod 18, an intermediate elongated rod 20 and a lower elongated rod 22. Rods 18, 20 and 22 are mounted so as to be axially slidable with respect to each other. This is accomplished by means of a forward bracket 24 and a rear bracket 26. Forward bracket 24 is bolted to the intermediate elongated rod 20 by bolts 30. Brackets 24 and 26 encompass the sides of upper and lower rods 18 and 22 and at least part of the bottom of lower rod 22 as is best seen in FIGS. 2 and 3. Thus, rods 18, 20 and 22 are restrained from movement other than axial movement with respect to each other. In view of the fact that brackets 24 and 26 are bolted to the intermediate elongated rod 20, rod 20 may be considered the stationary rod with rods 18 and 22 axially movable relative thereto.

The stapling portion 14 of the surgical stapler 10 is comprised essentially of a stapling head 32, an anvil 34 and an open ring shaped support structure 36. The rear end of the open ring shaped support structure 36 is rigidly connected to the upper elongated rod 18 and anvil 34 is rigidly supported at the other distal end of the support 36. Staple head 32 is rigidly supported by the forward end of the intermediate elongated rod 20 and as will be described in further detail below, the anvil 34 is movable toward and away from head 32. Both staple head 32 and anvil 34 have an ovoid cross-sectional shape which is most clearly seen in FIG. 5.

Referring again to FIGS. 1 and 2, it can be seen that the rearwardmost portion of upper elongated rod 18 is bent downwardly to form a flange 38. A thumb screw 40 has a shaft 42 journaled in an opening in flange 38. Shaft 42 is journaled into the opening in flange 38 in a known manner which allows rotational movement of the thumb screw 40 but wherein axial movement is prevented. The forward end of thumb screw 40 includes a threaded screw 44 which is adapted to mate with threaded bore 46 located at the rearwardmost end of intermediate elongated rod 20. It should now be readily apparent that by rotating thumb screw 40, upper elongated rod 18 is caused to move rearwardly or forwardly and as a result, anvil 34 carried by the rod 18 and open ring 36 can be made to move toward or away from staple head 32.

Handle portion 16 of the stapler 10 is comprised of two handle grips 48 and 50. Rear grip 48 is rigidly secured to the rear bracket 26 by bolts 52. Front handle grip 50, however, is pivotally mounted to rear bracket 26 at pivot point 54. Leaf spring 56 which is secured to front grip 50 and which rests against rear grip 48 biases the handle grips 48 and 50 away from each other. A locking pin 58 pivotally mounted to front handle grip 50 prevents movement of the handle grips 48 and 50 toward each other when pin 58 is in its locking position as shown in FIG. 1. Locking pin 58 is moved into its inoperative position by rotating the same in the direction of the arrow.

Front handle grip 50 includes a lower lever portion 62 extending beneath pivot point 54. Lever 62 passes through holes 64 and 66 in the upper elongated rod 18 and intermediately elongated rod 20, respectively, and terminates in a rounded end portion 68 which rests within opening 70 in lower elongated rod 22. It should be readily apparent that when handle grips 48 and 50 are moved toward each other, rounded end 68 of lever 62 moves forwardly or to the right as viewed in FIGS. 1 and 2 pushing lower elongated rod 22 forwardly along therewith. Similarly, when handle grips 48 and 50 move away from each other as a result of the tension of leaf spring 56, end portion 68 of lever 62 moves rearwardly or to the left as viewed in FIGS. 1 and 2 forcing lower elongated rod 22 to move rearwardly therewith. As will be described in more detail below, the forwardmost end of lower elongated rod 22 includes a pusher plate which effectuates the stapling operation.

Figure 6:
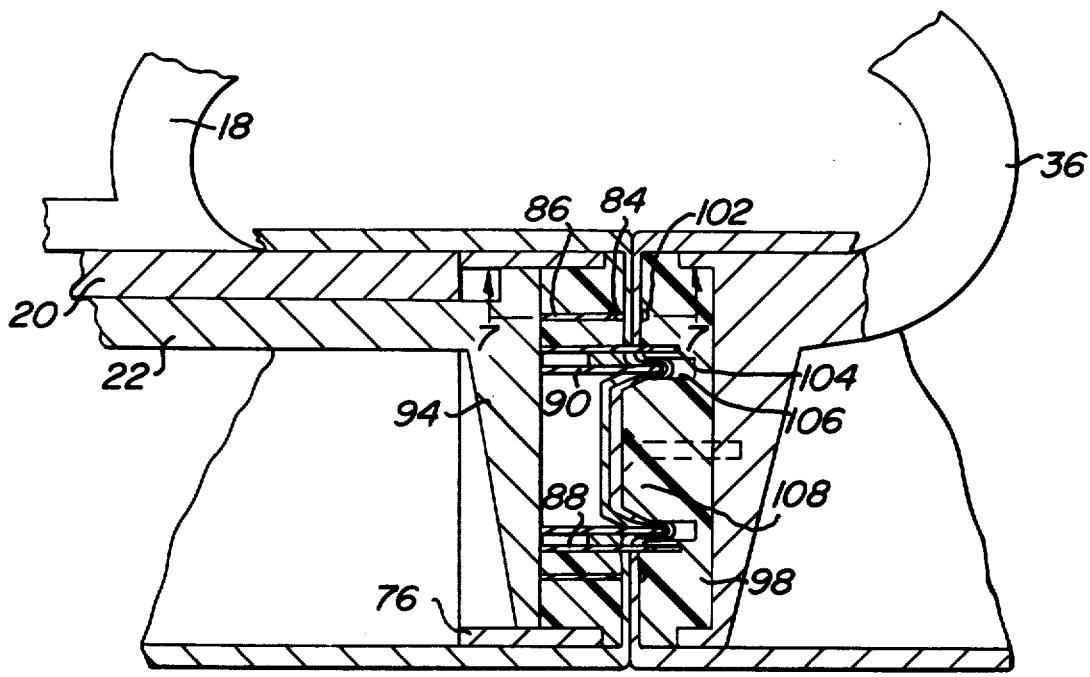
FIG. 6 is a view similar to FIG. 4 but showing the completion of a stapling and cutting operation.
Figure 5:
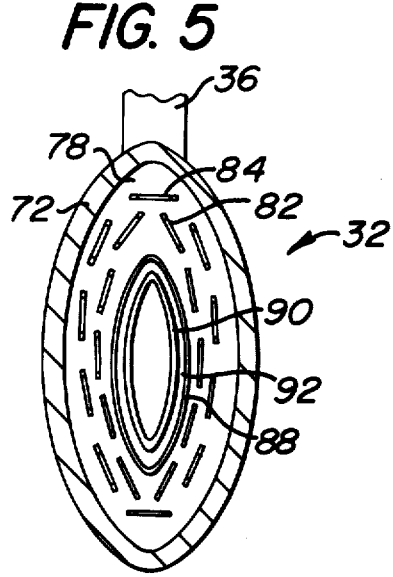
FIG. 5 is a sectional view taken along thhe line 5—5 of FIG. 4.

The staple head 32 and anvil 34 are shown in detail in FIGS. 4, 5 and 6. Referring first to FIG. 4, it can be seen that the stapler 10 is being employed to join together two bowel ends 72 and 74. In a manner which will be described in further detail below, the bowel ends 72 and 74 are first properly prepared and thereafter bowel end 72 is placed over the staple head 32 and bowel end 74 is placed over the anvil 34. Thumb screw 40 is then turned forcing staple head 32 toward anvil 34 to compress the tissue forcing staple head 32 toward anvil 34 to compress the tissue therebetween to approximately 50% of its original thickness. This is the position shown in FIG. 4.

Referring now to the staple head 32 in detail, it can be seen that the forwardmost end of intermediate elongated rod 20 terminates in a substantially cylindrically shaped housing 76 having an ovoid cross-section. Force fitted into the forward open end of housing 76 is a plastic insert 78 which also has an ovoid-shaped cross-section. A peripheral ridge 80 surrounding plastic insert 78 prevents rearward movement of insert 78 once it is properly placed within housing 76.

Spaced radially inwardly from the peripheral ridge 80, plastic insert 78 includes a plurality of openings 82. As shown best in FIG. 5, these openings 82 are arranged about the plastic insert 78 in the form of overlapping ovoid-shaped rows. Preloaded into each of the openings 82 is a stainless steel staple 84. And force fitted into the rear of each of the openings 82 is a staple driver 86. Staple drivers 86 extend rearwardly past the rear surface of plastic insert 78.

Plastic insert 78 is substantially ring-shaped having an inner surface which is substantially ovoid-shaped. Force fitted into the inner surface of plastic insert 78 is a cylindrically shaped stoma-forming cutting knife 88 which also has a ovoid-shaped cross-section. Cutting knife 88 is substantially longer in the axial direction than plastic insert 78 and extends rearwardly past the rear surface of insert 78. The forward portion of cutting knife 88 has a sharp edge and functions as the cutting edge of cutting knife 88.

Located radially inwardly from cutting knife 88 is a cylindrically shaped tensor ring 90. Tensor ring 90 also has an ovoid-shaped cross-section and is slightly longer in the axial length than cutting knife 88. A spacer ring 92 separates the cutting knife 88 from the tensor ring 90. The plastic insert 78, staples 84, staple drivers 86, knife 88, tensor ring 90 and spacer 92 are all pre-assembled thereby forming a removable and replaceable cartridge.

Also located within the cylindrically shaped housing 76 and rearwardly of the plastic cartridge 78 is pusher plate 94 referred to above. Pusher plate 94 has a substantially flat forward surface which is also ovoid-shaped and is rigidly secured to the lower elongated rod 22 for movement therewith. Pusher plate 94 acts on the tensor ring 90, cutting knife 88 and staple drivers 86 in a manner to be described below.

Referring now to the anvil 34 in detail, it can be seen in FIGS. 4 and 6 that anvil 34 is comprised of a rigid plate 96 secured to the distal end of open ring shaped support 36. Fitted into the rearwardly directed face of plate 96 is a or plastic insert 98. Insert 98 is secured to plate 96 by screw 100 which passes through the insert 98. As with the parts of the staple head 32, plate 96 and insert 98 of the anvil 34 have an ovoid cross-sectional shape.

The outer surface of insert 98 which faces rearwardly toward the staple head 32 includes a plurality of recesses 102. Recesses 102 are arranged about the insert 98 in double ovoid-shaped rows which correspond with the double ovoid-shaped rows of staples in the staple head 32. Recesses 102 are of a known configuration and serve to clinch the staples closed which are ejected from the staple head 32. Spaced radially inwardly from the rows of recesses 102 is an annular recess 104. Recess 104 has an ovoid configuration and lies directly opposite cutting knife 88 of staple head 32. Radially inwardly from recess 104 is a second annular recess 106. Recess 106 also has an ovoid configuration and lies directly opposite tensor ring 90 of staple head 32. Moving further radially inwardly, it can be seen that the central part of insert 98 has a raised portion such as shown at 108.

Figure 7:
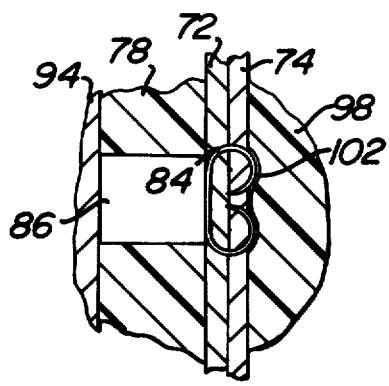
FIG. 7 is a partial sectional view taken along the line 7—7 of FIG. 6.

It should be readily apparent from FIG. 4 that when the handle grips 48 and 50 are closed, lower elongated rod 22 moves forwardly forcing pusher plate 94 to move forwardly or to the right thus contacting the rear edge of tensor ring 90. As pusher plate 94 continues to move forwardly, tensor ring 90 forces the tissue lying between the staple head 32 and the anvil 34 into the annular recess 106 thereby placing the tissue under tension. As pusher plate 94 continues its forward movement, it then engages the rear edges of cutting knife 88 and staple drivers 86. Further movement causes cutting knife 88 to extend forwardly of the plastic cartridge 78 thereby cutting into the tissue between the staple head 32 and anvil 34. At the same time, staple drivers 86 are moved forwardly forcing staples 84 into the tissue between the staple head and the anvil. In the final position shown in FIG. 6, the rear edges of the staple drivers 86, cutting knive 88 and tensor ring 90 are all in line with the rear surface of the plastic cartridge 78. The forward cutting edge of knife 88 has cut entirely through the tissue thereby forming an ovoid-shaped stoma therein and each of the staples has been clinched as shown in FIG. 7.

To complete the operation, the handle grip 50 is allowed to return to its open position thereby forcing the lower elongated rod and the pusher plate 94 rearwardly. Thereafter, thumb screw 40 is rotated thereby pushing forward the upper elongated rod 18 and the anvil therewith. The staple head 32 and anvil 34 are then removed from the interior of the bowels 72 and 74 and the end to end anastomosis is completed.

Figure 8:
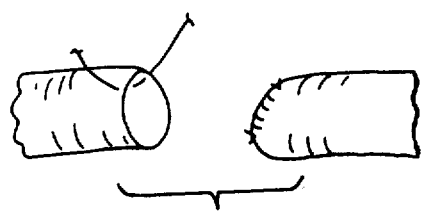
FIGS. 8-11 illustrate in substantially schematic form a complete end to end anastomosis performed by the stapler of the present invention.
Figure 9:
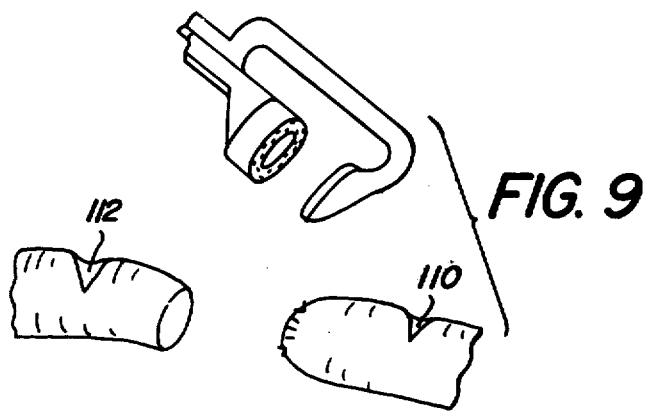

FIGS. 8–11 illustrate in substantially schematic form the manner in which the staple gun 10 of the present invention is utilized to perform an end to end anastomosis of bowel sections. As shown in FIG. 8, the first step is to suture closed the ends of each of the bowel sections 72 and 74. Thereafter, incisions 110 and 112 are made in each of the bowel sections adjacent the ends thereof. The anvil 34 is then introduced into the interior of bowel section 74 through the incision 110 and the staple head 32 is introduced into the interior of bowel section 72 through incision 112. It should be noted that the incisions 110 and 112 need not be very large since the anvil and staple head are ovoid-shaped and pass through the incisions along their shorter diameter. In contradistinction, prior art staplers required a substantially larger incision since the main body thereof which was inserted into the interior of the bowel was circularly and tubularly shaped.

Figure 10:
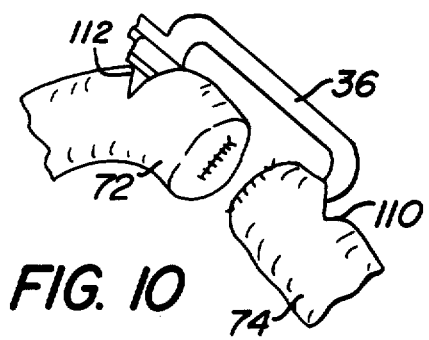
Figure 11:
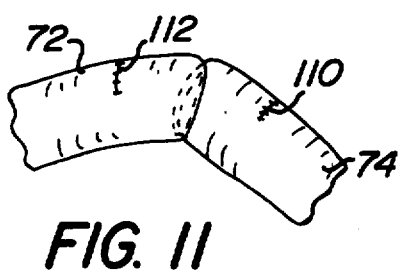

FIG. 10 shows the stapler inserted and properly positioned within the bowel ends. Once in this position, thumb screw 40 is turned thereby clamping the anvil against the staple head. Thereafter, the handles are closed putting the tissue between the staple head and anvil under tension, simultaneously inserting the double ovoid rows of staples and cutting away the interior portion of the bowels including that part which had been previously sutured to form a stoma. The staple head and anvil are then removed through the orginial incisions 110 and 112 and these incisions are sutured closed as shown in FIG. 11.

It should be readily apparent that the stapling operation described above can be performed relatively quickly. This is primarily true because of the fact that bowels are totally prepared before the stapler is positioned therein. Once the stapler is in position, nothing further need be done except to perform the stapling operation. Furthermore, in view of the fact that the staple head and the anvil are connected together by para-axial support structure externally of the bowels, the parts of the stapler being inserted into the bowel are relatively small thus making it substantially easier to maneuver the bowel and position it on the staple head and anvil. As a result, the ends of the bowel can be placed obliquely across the staple head and anvil if desired. By placing the bowel ends obliquely across the faces of the staple head and anvil, the stapler of the present invention can be used to perform anastomosis of bowels having various different cross-sectional diameters.

The present invention has been described with particular reference to end to end anastomosis. It should be readily apparent, however, that the device can also easily perform side to side, side to end and various other types of anastomosis. Further, while reference has been specifically made to the anastomosis of bowel sections, it should be readily apparent that the surgical stapler of the present invention is not limited thereto and can be used with substantially any hollow viscera.

The present invention may be embodied in other specific forms without departing from the spirit or essential attributes thereof and, accordingly, reference should be made to the appended claims, rather than to the foregoing specification as indicating the scope of the invention.

I claim:

1. A surgical stapler for intralumenal anastomosis comprising a staple head and an anvil; means supporting said staple head and said anvil for movement toward and away from each other; said staple head and said anvil each having an ovoid-shaped cross-section and being adapted to simultaneously set a plurality of staples in at least one row forming a closed loop.

2. A surgical stapler as claimed in claim 1 further including a stoma-forming knife mounted on said staple head, said knife generally conforming to and disposed within said row of staples.

3. A surgical stapler as claimed in claim 2 further including means mounted on said staple head and said anvil for tensioning the tissue to be cut by said knife.

4. A surgical stapler as claimed in claim 3 wherein said tensioning means includes a tensioning ring which generally conforms to and is disposed on said staple head within said stoma-forming knife which cooperates with a recess in said anvil.

5. A surgical stapler as claimed in claim 4 wherein said closed loop is ovoid-shaped and wherein said stoma-forming knife and said tensioning ring have an ovoid cross-sectional configuration.

6. A surgical stapler as claimed in claim 4 wherein said staple heads includes a removable and replaceable cartridge, said staples, knife and tensioning ring being carried by said cartridge.

7. A surgical stapler as claimed in claim 6 further including means associated with said staple head for moving said staples, knife and tensioning ring toward said anvil.

8. A surgical stapler as claimed in claim 7 wherein said anvil includes a plurality of recesses therein, said recesses cooperating with said staples, knife and tensioning ring.

9. A surgical stapler as claimed in claim 1 wherein said supporting means is substantially para-axially positioned with respect to said head and said anvil and is adapted to extend between said head and said anvil outside of the lumens being stapled.

10. A surgical stapler as claimed in claim 9 wherein said supporting means includes an open ring shaped structure, said staple head being mounted adjacent one end of said ring shaped structure and said anvil being mounted adjacent the other end thereof.

11. A surgical stapler for intralumenal anastomosis comprising a staple head and an anvil, said staple head and said anvil being adapted to simultaneously set a plurality of staples in at least one row to form a closed loop, and an open ring shaped support means supporting said staple head and said anvil for movement toward and away from each other, said staple head being mounted adjacent one end of said ring shaped support means and said anvil being mounted adjacent the other end thereof.

* * * * *